United States Patent [19]

Langlais et al.

[11] 4,173,797
[45] Nov. 13, 1979

[54] PROSTHESIS FOR ARTHROPLASTY OF THE HIP

[75] Inventors: Frantz Langlais; Michel Postel, both of Paris, France

[73] Assignee: Agence Nationale de Valorisation de la Recherche (ANVAR), Neuilly sur Seine, France

[21] Appl. No.: 825,384

[22] Filed: Aug. 17, 1977

[30] Foreign Application Priority Data

Aug. 19, 1976 [FR] France .................. 76 25215

[51] Int. Cl.² .............................................. A61F 1/24
[52] U.S. Cl. .................... 3/1.912; 128/92 C
[58] Field of Search .............. 3/1.912, 1.913, 1.9, 3/1.91; 128/92 C, 92 CA

[56] References Cited

U.S. PATENT DOCUMENTS

| 2,668,531 | 2/1954 | Haboush | 3/1.912 |
| 3,528,109 | 9/1970 | Scales | 3/1.91 |
| 4,051,559 | 10/1977 | Pifferi | 3/1.912 |

FOREIGN PATENT DOCUMENTS

| 1047640 | 7/1953 | France | 3/1.912 |
| 2297030 | 8/1976 | France | 3/1.912 |

OTHER PUBLICATIONS

McBride Acetabulum Cups, No. 6429 and Urist Hip Sockets, No. 6428, Vitallium Surgical Appliances (Catalog), Austenal Medical Division, Howmet Corp., N.Y., N.Y., p. 30, 1964 (received Jun. 9, 1966).

Primary Examiner—Ronald L. Frinks
Attorney, Agent, or Firm—Holman & Stern

[57] ABSTRACT

A hip prosthesis comprising a thin metal cotyloid cup, substantially spherical in form, the dimensions of the outer surface of which are substantially equal to those of a the cotyloid cavity, and which is provided with a peripheral flange for abutting on the bone around the cotyloid cavity and for preventing the cup from pivoting; a thin femoral cup, also made of metal, extended by a skirt and substantially in the form of a finger guard; and a relatively thick intermediate cup made of plastics material, having a spherical outer surface adapted to pivot in the cotyloid cup, and an inner surface comprising a spherical central part extended by a cylindrical portion which fits on the femoral cup so as to allow said latter to move only in rotation about the axis of symmetry of the cups.

8 Claims, 1 Drawing Figure

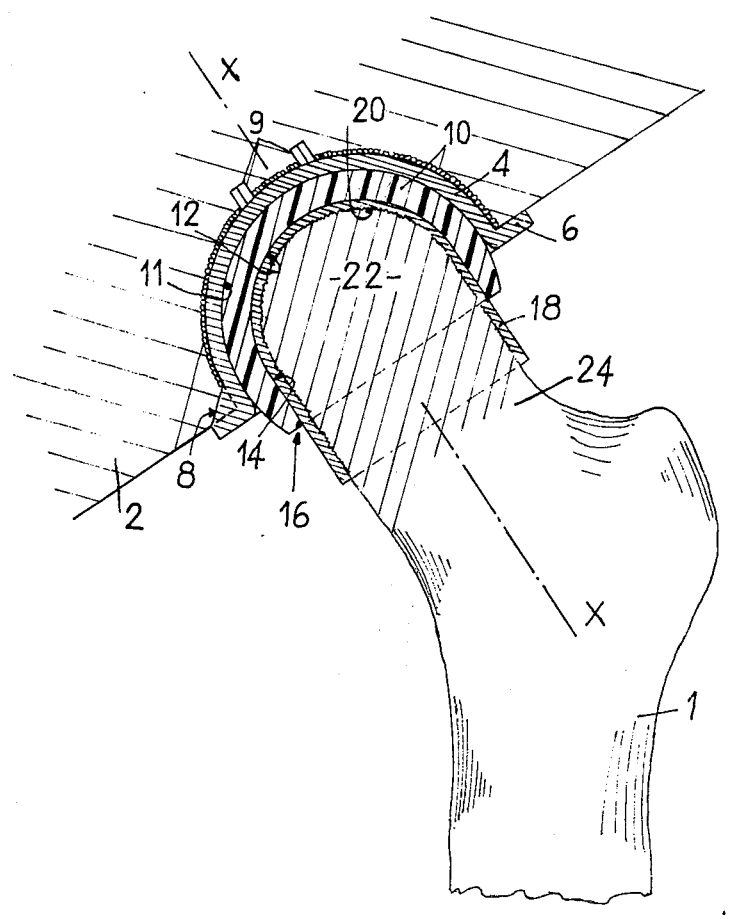

PROSTHESIS FOR ARTHROPLASTY OF THE HIP

The present invention relates to a prosthesis, particularly for arthroplasty of the hip. When the hip joint is considerably damaged by non-infectious lesions, the femoral and cotyloid articular surfaces are usually replaced either by a complete prosthesis or by using interconnected cups.

The complete prosthesis comprises a fixed cotyloid cup and a femoral head fast with a pin driven in the femur. It has two major drawbacks; the risk of the cotyloid part loosening due to the coefficient of friction of the prosthesis, and the serious consequences of an infection which must necessarily be treated by the total removal of the prosthesis, responsible for a considerable loss of bone substance.

The interconnected cups are composed of a femoral cup fitting on the head and neck of the femur and a cotyloid cup concentric with respect to the first and adapted to pivot in the cotyl, which is cut to accommodate said cotyloid cup. Such a prosthesis enables the neck of the femur and part of the femoral head to be conserved, this reducing the consequences of infection and conserving the physiological shock-absorber constituted by the femoral epiphysis. However, it often causes pain which appears to be associated with the mobility of the cotyloid cup in its cavity, which mobility is due, in axial rotation, to the high coefficient of friction for which the large diameter of the femoral cup is responsible, and to the fact that the movements of abduction and adduction of the hip cause the femoral cup to strike against the cotyloid cup.

It is an object of the present invention to remedy these drawbacks by proposing a prosthesis which enables the neck and femoral head to be conserved, and also reduces the risks of pain and limits the consequences of an infection due in particular to the fact that the elements fixed to the bone are subjected to little stain.

The invention therefore relates to a prosthesis which comprises a thin metal cotyloid cup, substantially spherical in form, the outer surface of which is a dimensions substantially equal to those of the cotyloid cavity, and which is provided with a peripheral flange for abutment on the bone around the cotyloid cavity and for preventing the cup from pivoting; a thin femoral cupule also made of metal, extended by a skirt member and substantially, in the form of a finger guard; and a relatively thick intermediate cup made of plastics material, having a spherical outer surface, adapted to pivot in the cotyloid cup, and an inner surface comprising a spherical central part extended by a cylindrical portion which fits on the femoral cup so as to allow said latter to move only in rotation about the axis of symmetry of the cup.

The movements of flexion-extension thus essentially provoke the displacement of the femoral cup in the intermediate cup and the movements of abduction-addution or rotation provoke the pivoting of the intermediate cup in the cotyloid cups, so that said latter remains fixed. Furthermore, the thick spherical form of the intermediate cup facilitates pivoting and avoids any danger of the femoral cup striking the cotyloid cup.

The invention will be more readily understood on reading the following description with reference to the accompanying drawings, in which:

The single FIGURE shows an axial section through the prosthesis according to the invention.

Referring now to the drawings, the single FIGURE shows a prosthesis for arthroplasty of the hip, in position of use between the end of a femur 1 and cotyl 2 cut to correspond to the prosthesis to be fitted. This prosthesis comprises a thin metal cup 4 in the form of a demisphere whose dimensions correspond to those of the cotyl 2, extended by a cylindrical annular edge 5 provided at its outer end with a flange 6 which abuts against the cotyloid supercillium, which is cut to this end. The outer surface of this cup 4 is rough and fits in the cotyl and is held therein either by being cemented or, preferably, by simply being force-fitted, the bone tissue being able subsequently to fill in the anfractuosities of the cup. The flange 6 prevents the cup from pivoting in the cotyl, whether the movement be inturned or in rotation in a horizontal plane.

In addition, the cup 4 comprises an outer boss 8 which cooperates with a corresponding recess in the lower wall of cotyl for immobilizing these two members with respect to each other in axial rotation, i.e. in rotation about axis X—X passing through the centre of the prosthesis and the axis of the neck of the femur 1.

An identical role may be played by several spikes 9 integral with the cup and projecting from its convex face, which prevent axial rotation where the osseous regrowth in the anfractuous coating has not yet taken over this immobilizing action. The spikes 9 can be used instead of the boss 8 or in combination therewith.

Inside the cup 4 is mounted an intermediate cup 10 made of plastics material, the outer surface 11 of which is spherical and concentric with respect to cup 4, whilst its inner surface comprises a spherical central part 12, extended by a cylindrical portion 14. This intermediate cup 10 is thicker than the cup 4, as is clearly shown in the drawing.

The inner cavity of cup 10 contains a third or femoral cup 16, in the form of a finger guard, which, like cup 4, is made of metal and is relatively thin. The outer surface of this cup 16 corresponds substantially to the inner cavity of the cup 10 in which it is fitted. Its end is therefore hemispherical, concentric to the cup 4 and to the cotyl 2, and is extended by a lateral skirt member 18.

The inner surface 20 of this cup 16 is rough and is closely fitted on the head 22 of the femur 1, the skirt member 18 extending in the direction of the neck 24 of said femur and fitting thereon.

Due to the relative shape of the cups 16 and 10, cup 16 may rotate in cup 10 about the axis of the neck of the femur, this corresponding to the preponderant mobility when walking, but cannot move in any other manner. Its finger-guard shape enables it to have a small external diameter, so that the torque with the intermediate cup is reduced.

The spherical cup 10 pivots in the cup 4, which is also spherical, to ensure inturning and horizontal rotation. It may also rotate about the axis of the neck of the femur, but on these large surfaces, the torque is greater than on the smaller inner surface. These movements are therefore preferably made between the inner, fingerguard shaped surface and the cup 16. Only the inturning and horizontal rotation movements, less used physiolocally, are made between the two spherical surfaces, with the result that the cotyloid cup is subjected to little strain, whilst in the usual movements the torque is particularly low. The low coefficient of friction between the plastics material of the intermediate cup and the metal of the femoral and cotyloid cups facilitates these movements.

A prosthesis is therefore obtained which enables the neck and head of the femur to be conserved and in which, as the elements fixed to the bone, i.e. the cotyloid cup, are subject to little strain, the risks of displacement and loosening are reduced.

The considerable thickness of the intermediate cup avoids any risk of creeping. In addition, as the femoral cup is thin and consequently has an external diameter only a little larger than that of the head of the femur whilst the intermediate cup is thick with the result that its outer spherical surface has a clearly larger diameter, the femoral cup may move through a relatively large angle without abutting against the cotyloid cup. An appropriate choice of the diameters of the cups gives the femoral cup some play with respect to the cotyloid cups which is greater than that required by the usual movements, this further reducing the risk of loosening and eliminating an important cause of pain.

Having now described our invention what we claim ad new and desire to secure by Letters Patent is:

1. A prosthesis for arthroplasty of the hip, which comprises:
   a thin metal cotyloid cup of hemispherical shape to be fitted in the cotyloid cavity and having an outer surface which has dimensions substantially equal to those of the cotyloid cavity and having a peripheral flange for abutting on bone around the cotyloid cavity for preventing the cup from pivoting relative to cotyloid cavity;
   a thin femoral cup of metal having a cylindrical skirt portion to be fitted on the head of the femur;
   and an intermediate cup of plastics material which is thicker than said cotyloid cup and said femoral cup and has a part-spherical outer surface which is such that when the intermediate cup is mounted in the cotyloid cup it is capable of swivelling in all directions relative to the cotyloid cup, the intermediate cup having an inner surface which comprises a cylindrical portion which fits coaxially on the cylindrical skirt portion of the femoral cup so as to allow the femoral cup only a movement of rotation about the common axis of the skirt portion and cylindrical portion.

2. The prosthesis of claim 1, wherein the outer surface of the cotyloid cup to be in contact with the surface of the cotyloid cavity is rough and said cotyloid cup is sized for fixing in said cotyloid cavity by force-fitting.

3. The prosthesis of claim 1, wherein the outer surface of the cotyloid cup to be in contact with the surface of the cotyloid cavity is rough and said cotyloid cup is adapted to be fixed in said cotyloid cavity by means of cement.

4. The prosthesis of claim 1, wherein the inner surface of the femoral cup which is adapted to be fixed on the head and neck of the femur is rough.

5. The prosthesis of claim 1, wherein the cotyloid cup comprises an outer boss for cooperating with the cotyloid cavity in a recess made therein in order to prevent the cotyloid cup from rotating about its center in a plane containing said flange.

6. The prosthesis of claim 1, wherein the outer surface of the colyloid cup comprises metal spikes adapted to penetrate the cotyl.

7. A prosthesis for arthroplasty of the hip, which comprises:
   a thin metal cotyloid cup of hemispherical shape to be fitted in the cotyloid cavity and having an outer surface which has dimensions substantially equal to those of the cotyloid cavity and having a peripheral flange for abutting on bone around the cotyloid cavity for preventing the cup from pivoting relative to cotyloid cavity;
   a femoral member of metal having a hemispherical portion and a cylindrical portion and to be mounted on the femur;
   and an intermediate cup of plastics material which is thicker than said cotytloid cup
   and has a part-spherical outer surface which is such that when the intermediate cup is mounted in the cotyloid cup it is capable of swiveling in all directions relative to the cotyloid cup, the intermediate cup having an inner surface which comprises a hemispherical portion which is extended by a cylindrical portion which fits coaxially on the cylindrical portion of the femoral member so as to allow the femoral member only a movement of rotation about the common axis of the cylindrical portions.

8. The prosthesis of claim 7, wherein the hemispherical shapes of the cotyloid and intermediate cups and femoral member are concentric with respect to one another.

* * * * *